United States Patent [19]

Freerks

[11] 4,304,723

[45] Dec. 8, 1981

[54] PROCESS FOR MANUFACTURING MALEIC ANHYDRIDE

[75] Inventor: Marshall C. Freerks, Kirkwood, Mo.

[73] Assignee: Monsanto Company, St. Louis, Mo.

[21] Appl. No.: 189,535

[22] Filed: Sep. 22, 1980

[51] Int. Cl.$^3$ ............................................. C07D 307/60
[52] U.S. Cl. ................................. 260/346.75; 252/432
[58] Field of Search ..................................... 260/346.75

[56] References Cited

U.S. PATENT DOCUMENTS

| | | | |
|---|---|---|---|
| 3,856,824 | 12/1974 | Raffelson et al. | 260/346.75 |
| 4,018,709 | 4/1977 | Barone et al. | 252/437 |
| 4,052,418 | 10/1977 | Suresh et al. | 260/346.75 |

*Primary Examiner*—Henry R. Jiles
*Assistant Examiner*—Bernard Dentz
*Attorney, Agent, or Firm*—Thomas Y. Awalt, Jr.

[57] ABSTRACT

Catalyst activity is substantially increased in phosphorus-vanadium-oxygen catalysts for the preparation of maleic anhydride from saturated hydrocarbons having 4 to 10 carbon atoms by the addition of boron to the catalyst composition.

7 Claims, No Drawings

PROCESS FOR MANUFACTURING MALEIC ANHYDRIDE

FIELD OF THE INVENTION

This invention relates to a process for the manufacture of dicarboxylic acid anhydrides by the oxidation of hydrocarbons. More particularly, it is directed to a process suitable for producing maleic anhydride from saturated hydrocarbons in higher yields than heretofore possible.

Maleic anhydride is of significant commercial interest throughout the world. It is used alone or in combination with other acids in the manufacture of alkyd and polyester resins. It is also a versatile intermediate for chemical synthesis. Significant quantities of maleic anhydride are produced each year to satisfy these needs. The prior art discloses a number of processes used in the conversion of organic feedstocks to maleic anhydride.

Of particular interest is U.S. Pat. No. 3,293,268 which teaches a process of oxidizing saturated aliphatic hydrocarbons to maleic anhydride under controlled temperature conditions and in the presence of phosphorus-vanadium-oxygen catalysts. Through various improvements including the use of promoters such as cobalt, nickel and cadmium, yields have been substantially increased, as exemplified in U.S. Pat. No. 4,111,963 and U.S. Pat. No. 3,987,063.

Any economically feasible method of substantially reducing the operating temperature or increasing the level of selectivity in the manufacture of maleic anhydride including alternative methods to those already known could be a substantial advance in the art and is an object of this invention.

SUMMARY OF THE INVENTION

These and other objects are achieved in a process for preparing maleic anhydride wherein a mixture of an oxygen-containing gas and a saturated hydrocarbon having 4 to 10 carbon atoms is contacted with a catalyst complex comprising phosphorus, vanadium and oxygen, the improvement wherein the complex also comprises boron.

In the ordinary practice of this invention, the mixture of oxygen-containing gas and the hydrocarbon are reacted at about 350°–360° C. The phosphorus-to-vanadium atom ratio of the catalyst is about 1:2 to about 2:1. At least 50 atom % of the vanadium is in the tetravalent state. An effective amount of the boron can be any amount which reduces the required operating temperature or increases the selectivity in the manufacture of maleic anhydride. A typical boron/vanadium atom ratio, as will be seen in the examples, is 0.01.

For the purposes of this invention, the term "catalytic activity" means the ability to convert a particular feedstock, such as butane, at a particular temperature to other compounds. The term "selectivity" means the ratio of the moles of maleic anhydride obtained to the moles of hydrocarbon reacted. The term "yield" means the ratio of the moles of maleic anhydride obtained to the moles of hydrocarbon introduced into the reaction. The term "space velocity" means the hourly volume of the gaseous feed expressed in cubic centimeters (cc) at 60° F. and standard atmospheric pressure divided by the catalyst bulk volume expressed in cubic centimeters (cc), the term expressed as cc/cc/hour.

Broadly described, the catalysts used in the process of this invention to convert saturated hydrocarbons to maleic anhydride are prepared by contacting vanadium compounds, phosphorus compounds, and the boron or a boron compound under such conditions that a substantial amount of tetravalent vanadium is provided to form catalyst precursors, recovering the catalyst precursors, forming the catalyst precursors into structures for use in a maleic anhydride reactor, and calcining the structured catalyst precursors to form the catalysts.

The vanadium compounds useful as a source of vanadium in the catalyst precursors are those known to the art to be useful for preparing catalysts to oxidize hydrocarbons. Suitable vanadium compounds include: vanadium oxides, such as vanadium pentoxide, vanadium trioxide, and the like; vanadium oxyhalides, such as vanadyl chloride, vanadyl trichloride, vanadyl dichloride, vanadyl bromide, vanadyl dibromide, vanadyl tribromide, and the like; vanadium salts, such as ammonia metavanadate, vanadium sulfate, vanadium phosphate, vanadyl formate, vanadyl oxalate and the like. However, vanadium pentoxide is preferred.

As a source of phosphorus in the catalyst precursors, useful phosphorus compounds are also those well known in the art useful for preparing catalysts to oxidize hydrocarbons. Suitable phosphorus compounds include: phosphorus acid, phosphoric acids, such as metaphosphoric acid, othophosphoric acid, triphosphoric acid, pyrophosphoric acid, and the like; phosphorus oxides, such as phosphorus pentoxide and the like; phosphorus halides, such as phosphorus oxyiodide, phosphorus pentachloride, phosphorus oxybromide and the like; and organophosphorus compounds such as ethyl phosphate, methyl phosphate and the like. However, phosphorous acid is preferred.

The compound or compounds used to introduce the boron component include metallic boron or any boron compound in which boron exists or from which boron may evolve. The compound must, however, be a non-interfering compound in the sense that in either ionized or deionized form it does not substantially interfere with the production of the catalyst precursor or catalyst, or with the production of maleic anhydride. Boric acid is preferred. The boron compound may be introduced into the catalyst at any stage of catalyst preparation prior to calcining the catalyst. Preferably, the boron compound is introduced into the catalyst precursor at the initial stages of the precursor formation in the amount of about 3–10 atom % based on vanadium (boron/vanadium atom ratio of 0.03–0.1), more preferably about 5%.

To prepare precursors to the catalysts used in the present process, a pentavalent or tetravalent vanadium compound is heated with a phosphorus compound in an acid solution to dissolve the starting materials. A mild reducing agent is used to provide tetravalent vanadium and/or to maintain vanadium in the tetravalent state. On the other hand, an acid with reducing properties, such as hydrogen halide acid or oxalic acid, can serve as the acid and can provide tetravalent vanadium. Phosphorous acid is preferred. The acid solution containing the phosphorus compound and the vanadium compound are heated until a blue solution is obtained, indicating that a substantial amount, i.e., greater than 50 atom percent, of the vanadium is in the tetravalent state. The amount of time required to dissolve the phosphorus and vanadium compounds and to provide a substantial amount of the vanadium in the tetravalent state to form the catalyst precursors varies from batch to batch, depending upon the compounds used as starting materials and the temperature at which the compounds are heated. However, as will occur to those skilled in the art, the solution can be analyzed to insure that most of the vanadium is in the tetravalent state.

Although any number of phosphorus and vanadium compounds can be used to form the precursor, the atom ratio of phosphorus to vanadium in the precursor is important, since it controls the phosphorus-to-vanadium atom ratio in the final catalyst. When the precursor contains a phosphorus to vanadium atom ratio below about 1:2 or above about 2:1, the yield of maleic anhydride using the process of this invention is so low that it is not of commercial significance. It is preferred that the precursors have a phosphorus to vanadium atom ratio in the range of about 1:1 to about 1.5:1. When the catalyst is used to convert a feed that is primarily butane to maleic anhydride, it is even more preferable to have a phosphorus to vanadium atom ratio of about 1:1 to about 1.2:1, say about 1.1:1.

After the precursors have been formed by heating the vanadium compounds and the phosphorus compounds, and a substantial amount of vanadium has been reduced to the tetravalent state, it is necessary to remove most of the water in order to recover the precursor. Techniques for recovering the precursors from solution are well known to those skilled in the art. Precursors can be deposited on a carrier, such as alumina or titania, from solution, or excess water can be removed to provide the precursors.

After the precursors are recovered from solution, they are then formed into structures suitable for use in a maleic anhydride reactor. Techniques for forming appropriate structures from the precursors for use in a fluidized bed reactor or in a fixed tube, heat exchanger type reactor are well known to those skilled in the art. For example, the precursors can be structured for use in a fluidized bed reactor by depositing the precursors from solution on a carrier, or alternatively, the dried precursors can be comminuted for use in a fluidized bed reactor. On the other hand, the precursors can be structured for use in a fixed tube reactor by prilling or tabletting the precursors.

After the precursors have been formed into the structures in which they will be used in the maleic anhydride reactor, they can be calcined in an oxygen-containing atmosphere, such as air, at temperatures of from about 350° C. to about 600° C. for at least about 2 hours to convert the precursors to the catalysts for use in the present process.

If more than about 90 atom percent of the vanadium is oxidized to pentavalent vanadium, usually caused by calcining in air at too high a temperature, the selectivity of the catalyst and the yield of maleic anhydride decrease markedly. On the other hand, oxidation of less than about 20 atom percent of the vanadium during air calcination does not seem to be more beneficial than calcination in an inert atmosphere.

After the precursors have been calcined to form the catalysts of this process, the catalysts can be used to convert a saturated hydrocarbon to maleic anhydride. However, the initial yield of maleic anhydride may be low, and if this is the case, the catalysts can be conditioned, as will occur to those skilled in the art by passing low concentrations of a saturated hydrocarbon in air through the catalyst for a period of time before production operations begin.

After the catalysts of the present process have been used about 16 hours to prepare maleic anhydride from a mixture of about 1.5 atom percent saturated hydrocarbon, such as butane, at a space velocity of about 1500 cc/cc/hour at a temperature of 400°–440° C., a substantial amount, i.e., greater than 50 atom percent of the vanadium in the catalyst is in the tetravalent state, as determined by the tetravalent vanadium test hereinafter described. When the catalysts contain less than about 50 atom percent vanadium in the tetravalent state, the catalyst is too unselective to be used for the oxidation of saturated hydrocarbons to maleic anhydride.

In the tetravalent vanadium test, a sample of the catalyst is dissolved in dilute acid, and thereafter, the tetravalent vanadium is titrated with a standardized permanganate solution in a first titration. The pentavalent vanadium is then reduced to the tetravalent state by the addition of sodium sulfite and the vanadium is titrated with the standardized permanganate solution in a second titration. The percent tetravalent vanadium can be calculated from the differences between the two values.

The catalysts of the present process are useful in a variety of reactors to convert saturated hydrocarbons to maleic anhydride. Both fluidized bed reactors and fixed tube heat exchanger type reactors are satisfactory and details of the operation of such reactors are well known to those skilled in the art. The reaction to convert saturated hydrocarbons to maleic anhydride requires only contacting the saturated hydrocarbon admixed with a free-oxygen containing gas, such as air or oxygen-enriched air, with the catalysts at elevated temperatures. The saturated hydrocarbons are contacted with the catalysts at a concentration of about 1.5 to about 10 volume percent saturated hydrocarbons at a space velocity of about 100 to 4,000 cc/cc/hour to provide maleic anhydride yields of greater than 40% at temperatures between about 350° C. and 600° C.

The catalysts of the present process are particularly useful in fixed tube heat exchanger type reactors. The tubes of such reactors can vary in diameter from about ¼ inch to about 1.5 inches and the length can vary from about 6 inches to about 10 or more feet. It is desirable to have the surfaces of the reactors at relatively constant temperature, and some medium to conduct heat from the reactors is necessary to aid temperature control. Such media can be Woods metal, molten sulfur, mercury, molten lead and the like or eutectic salt baths. A metal block reactor whereby the metals surrounding the tube act as a temperature regulating body can also be used. The reactor or reaction tubes can be iron, stainless steel, carbon steel, glass and the like.

Maleic anhydride prepared by using the process of this invention can be recovered by any number of means well known to those skilled in the art. For example, the maleic anhydride can be recovered by direct condensation or by absorption in suitable media with subsequent separation and purification of the anhydride.

The pressure in the reactor is not generally critical. Therefore, the reaction can be run at atmospheric, superatmospheric and subatmospheric pressures, although superatmospheric pressures are usually employed.

A large number of saturated hydrocarbons having from 4 to 10 carbon atoms can be converted to maleic anhydride using the process of the present invention. It is only necessary that hydrocarbons contain not less than 4 carbon atoms in a straight chain. As an example, the preferred saturated hydrocarbon is butane, but isobutane which does not contain 4 carbon atoms in a straight chain is not satisfactory for conversion to maleic anhydride, although its presence is not harmful. In addition to butane, other saturated hydrocarbons within the scope of this invention include the pentanes, the hexanes, the heptanes, the octanes, the nonanes, the decanes, or mixtures of any of these with or without butane. In addition to the above compounds, cyclic compounds such as cyclopentane or cyclohexane are satisfactory feed materials for conversion to maleic anhydride. Also, the feedstock can be technical grade hydrocarbons containing up to about 25 weight percent of olefinically unsaturated hydrocarbons or other hydrocarbon fractions.

The principal product from the oxidation of the above feed materials is maleic anhydride. It should be noted that small amounts of citraconic anhydride may also be produced when the feedstock is a saturated hydrocarbon containing more than 4 carbon atoms.

DESCRIPTION OF THE PREFERRED EMBODIMENT

The invention is further illustrated, but not limited to the following examples:

EXAMPLE 1

The following was charged to a 1-liter autoclave in the order given:
107.76 g of $H_3PO_4$ (85%)
84.31 g of $H_3PO_3$
575 cc deionized water (DI)
170 g of $V_2O_5$
5.68 g of $H_3BO_3$
(providing a B/V atom ratio of 0.05).

The contents of the autoclave were heated to 155° C., which temperature was maintained for four hours after which the autoclave was cooled to 88° C.; then placed in an oven at 125° C. overnight. The blue catalyst precursor was ground to pass an 18-mesh screen; then tabletted to a 4.76 mm-diameter tablet 4.75–4.79 mm in length, using 0.5% STEROX ® tabletting lubricant manufactured by Monsanto. The tablets were then calcined at 400° C. for six hours in air. The calcined tablets were charged to a maleic anhydride reactor in the manner explained above. A control catalyst without the boron compound, but in other respects identical was also charged to a similar reactor. The results are shown below.

EXAMPLE 2

The following was charged to a 2-liter autoclave in the order given:
600 cc Di $H_2O$
340.0 g $V_2O_5$
215.5 g 85% $H_3PO_4$ solution
170.8 g of $H_3PO_3$, 99.3%
11.56 g of $H_3BO_3$
550 cu DI $H_2O$.

(Providing a B/V atom ratio of equal to or greater than 0.05 and a P/V atom ratio of equal to or greater than 1.06).

The contents of the autoclave were heated as in Example 1 and the catalyst precursor was treated as in Example 1 except that graphite rather than STEROX ® tabletting lubricant was used.

EXAMPLE 3 (COMPARATIVE)

The catalyst was prepared in the same manner as Example 2 except that no boric acid was included in the charge to the autoclave.

The performance of the catalyst of Examples 1–3 in a preparation of maleic anhydride from butane is shown on the following table reflecting comparable yields at substantially lower operating temperatures where boric acid was added to the catalyst.

TABLE I

| Example | Reactor Length Ft. | Butane Feed Conc. % | Space Velocity $hr^{-1}$ | Bath Temp °C. | % Yield |
|---|---|---|---|---|---|
| 1 | 0.5 | 1.86 | 1540 | 363 | 48.6 |
| 2 | 4.0 | 1.50 | 1450 | 393 | 54.5 |
| 3 | 4.0 | 2.00 | 1450 | 413 | 48.9 |

I claim:
1. In a process for preparing maleic anhydride, wherein a mixture of an oxygen-containing gas and a saturated hydrocarbon having 4 to 10 carbon atoms in vapor phase is contacted with a catalyst complex comprising phosphorus, vanadium, and oxygen, the improvement wherein the complex also includes boron in an amount sufficient to substantially increase activity of the catalyst the said catalyst complex consisting essentially of phosphorus at a phosphorus-to-vanadium atom ratio of about 1:2 to about 2:1, vanadium, oxygen and boron at an atomic ratio of boron to vanadium of about 0.03–0.10.

2. The process of claim 1 wherein the oxygen-containing gas is air.

3. The process of claim 1 wherein the saturated hydrocarbon is butane.

4. The process improvement of claim 1 wherein the catalyst has a phosphorus to vanadium atom ratio in the range of about 1:1 to about 1.2:1.

5. The process improvement of claim 1 wherein the catalyst has a boron-to-vanadium atom ratio of about 5%.

6. The process of claim 1 wherein the catalyst complex is the product of the process comprising:
(a) contacting vanadium and phosphorus compounds, and a compound containing boron under conditions which will provide a catalyst precursor wherein greater than 50% of the vanadium is tetravalent vanadium;
(b) recovering the catalyst precursor;
(c) forming the catalyst precursor into structures and,
(d) calcining the catalyst precursors.

7. The process of claim 6 wherein the compound containing boron is boric acid.

* * * * *